United States Patent [19]

Cyrus et al.

[11] 4,088,763
[45] May 9, 1978

[54] ALKYLENEDIOXY PIPERAZINE DERIVATIVES

[75] Inventors: Richard Cyrus, Ludwigshafen; Manfred Raschack, Weisenheim am Sand, both of Germany

[73] Assignee: Knoll A.G. Chemische Fabriken, Ludwigshafen (Rhine), Germany

[21] Appl. No.: 760,557

[22] Filed: Jan. 19, 1977

[30] Foreign Application Priority Data

Feb. 7, 1976 Germany .............................. 2604838

[51] Int. Cl.² .................. A61K 31/495; C07D 241/04
[52] U.S. Cl. .................................... 424/250; 544/377; 544/401; 544/384; 544/396
[58] Field of Search ................. 260/268 BC; 424/250

[56] References Cited

U.S. PATENT DOCUMENTS 3,119,826  1/1964  Regnier et al. ................ 260/268 BC
3,681,359  8/1972  Leigh et al. ................... 260/268 BC

OTHER PUBLICATIONS

Elderfield, Heterocyclic Compounds, vol. 6, pp. 70 & 448, pub. by John Wiley & Sons, 1957.

*Primary Examiner*—Paul M. Coughlan, Jr.
*Attorney, Agent, or Firm*—Curtis, Morris & Safford

[57] ABSTRACT

Alkylenedioxy piperazine compounds of the formula

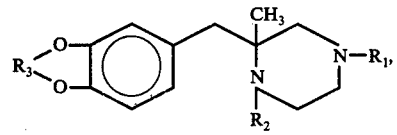

and salts thereof with physiologically tolerated acids, useful for the treatment of vascular and cardiac diseases, are disclosed, as are methods for making the compounds and pharmaceutical compositions containing the compounds.

76 Claims, No Drawings

ALKYLENEDIOXY PIPERAZINE DERIVATIVES

The present invention relates to alkylenedioxy piperazine derivatives, to methods for their preparation, and to pharmaceutical compositions containing these compounds.

It is known that life-threatening ventricular disturbances of the cardiac rhythm and coronary cardiac diseases often occur within a narrow time span or are linked by a common cause [cf. F. Nager et al., Schweiz. med. Wschr. 102, 1836 – 1851 (1972)]. The medicaments which are available for the treatment of symptoms of this kind either are effective against only cardiac arrhythmia (e.g. Lidocain) or only against coronary pain (e.g. nitroglycerin).

The present invention relates to alkylenedioxy piperazine derivatives of the formula

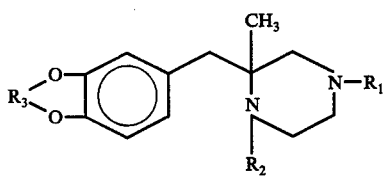

wherein $R_1$ is hydrogen or diphenylmethyl or diphenylmethyl in the phenyl groups of which a hydrogen atom may be replaced by halogen, $R_2$ is hydrogen or hydrocarbon having 1 to 5 carbon atoms, which hydrocarbon may be substituted by amino or hydroxy, and $R_3$ is methylene or ethylene, as well as salts thereof with physiologically tolerable acids.

The invention further relates to a method for the preparation of alkylenedioxy piperazine derivatives of the aforementioned formula, as well as salts thereof with physiologically tolerable acids, which comprises a. reducing a compound of the formula

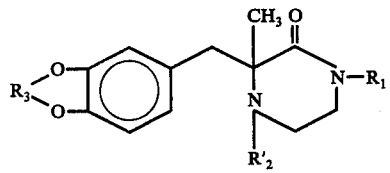

wherein $R_1$ and $R_3$ are the same as described above and $R'_2$ is the same as $R_2$ or is benzyl or acyl, with a metalloorganic compound. In case $R'_2$ is benzyl, the latter is removed by hydrogenation; or b. reacting a compound of the formula

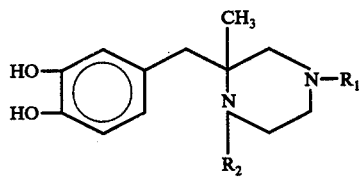

wherein $R_1$ and $R_2$ are the same as described above with an alkylene dihalide. In case $R_1$ and/or $R_2$ are hydrogen in the compounds so obtained, a substituent can optionally be introduced onto the nitrogen atom. The substances so obtained are, if desired, converted into their salts with physiologically tolerable acids.

Finally, the present invention relates to pharmaceutical compositions which contain compounds of the aforementioned formula on their salts with physiologically tolerable acids. As physiologically tolerable acids hydrochloric acid, sulfuric acid, phosphoric acid, acetic acid, malonic acid, succinic acid, citric acid, tartaric acid, lactic acid, and diamidosulfonic acid come into consideration, among others.

The reduction of the piperazinone derivatives to the corresponding piperazines can be carried out with complex hydrides such as lithium aluminum hydride or dibutyl aluminum hydride, in ethers, preferably diethyl- or diisopropyl- ether, or in cyclic ethers such as tetrahydrofuran or dioxane. It is recommended to work at higher temperatures, preferably at the boiling temperature of the solvents employed.

The alkylation of the piperazine ring system with substituted or unsubstituted diphenylmethyl halides takes place specifically at the nitrogen atom in the 1-position. As halides, the bromides and chlorides preferably are employed. As solvents, aromatic hydrocarbons such as benzene, toluene, and xylene, or lower boiling ketones such as acetone, methylethyl ketone, or diisobutyl ketone are employed. Also suitable are, for example, dimethylformamide and hexamethylphosphoric acid triamide. The temperatures are preferably between 25° C. and 130° C. It is recommended to add basic condensation agents such as tertiary organic bases or alkali carbonates such as potassium carbonate or sodium carbonate.

An alkylation of the nitrogen atom in the 4-position can take place in an analogous fashion. When using alkyl chlorides or alkyl bromides, however, the addition of sodium iodide or potassium iodide and the use of a small excess pressure of about 1.5–10 atmospheres gauge is recommended.

The possibility further exists of acylating the piperazine ring system at the nitrogen atom in the 4-position with acyl halides, anhydrides, or esters and reducing the acylation products is aliphatic or cyclic ethers —such as diethyl ether, dioxane, or tetrahydrofuran— by means of complex hydrides to form the corresponding alkyl derivatives.

A methyl group can also be introduced onto the nitrogen atom in the 4-position by reacting the piperazine in suitable solvents, for example aromatic hydrocarbons or halohydrocarbons, in the presence of a base, preferably triethylamine, with a haloformic acid ester at low temperatures. The acylation products so obtained can be reduced very readily in a known fashion with complex hydrides.

The reaction with acylating agents can also be carried out already with the piperazinones. In the reduction of the CO-group in the 2-position, an acyl group in the 4-position is also reduced and converted to an alkyl group.

The piperazine derivatives can further be hydroxyalkylated with alkylene oxides at the nitrogen atom in the 4-position. Mixtures of low boiling alcohols and aromatic hydrocarbons preferably methanol and benzene in a ratio of 2:1, serve as the solvent. The reaction is suitably carried out at temperatures of 25° – 80° C. and at a pressure of 3 – 5 atmospheres.

In these reactions at the 4-nitrogen atom, the nitrogen atom in the 1-position must either already be substituted by group $R_1$ or by a protective group, which later is cleaved, since otherwise the same reaction would occur at the 1-nitrogen atom as occurs at the 4-nitrogen atom.

The reaction of 3,4-dihydroxybenzyl-compounds to the corresponding alkylenedioxybenzyl-compounds is carried out in aprotic solvents such as dimethylformamide, hexamethylphosphoric acid triamide, and sulfolane. Dimethylsulfoxide is particularly suitable. As alkylation agents, halohydrocarbons such as 1,2-dihaloethanes, and dihalomethanes are employed. It is recommended to work in the presence of basic condensation agents such as alkali metal hydroxides and alkali metal carbonates. The addition of copper powder is an advantage. The reaction temperatures are about 40° – 150° C.

This same reaction can also be carried out by means of phase-transfer catalysis in aromatic hydrocarbons such as benzene, toluene, and xylene, or in cyclic ethers, such as tetrahydrofuran and dioxane. As catalysts, quaternary alkyl ammonium halides having longer alkyl chains are suitable. The reaction is preferably carried out at about 20° – 100° C. with dibromomethane or 1,2-dibromoethane in the presence of basic condensation agents such as alkali hydroxides.

The new compounds have good anti-arrhythmic efficacy. Further, even in small doses they antagonize the vasoconstricting effects of calcium ions on the arterial vessel muscles. Thus, they are particularly suitable for the treatment of coronary cardiac diseases and the disturbances of the cardiac rhythm which are associated therewith.

Further, the new compounds inhibit the vasoconstricting effects of numerous biogenic amines so that they can be used for the treatment of vascular diseases such as high blood pressure and peripheral and cerebral circulatory disturbances.

As the following Table shows, the new compounds inhibit the vasoconstricting effects of numerous biogenic amines and other vasoconstrictors.

TABLE 1

| Substance | Dose (M) | A Histamine | A Adrenalin | B Calcium | C Serotonin |
|---|---|---|---|---|---|
| I | $10^{-7}$ | – 41% | – 83% | – 30% | – 40% |
| II | $10^{-7}$ | – 27% | – 58% | – 26% | – 27% |
| III | $10^{-7}$ | – 43% | – 56% | – 16% | – 6% |
| IV | $10^{-7}$ | – 12% | – 65% | – 20% | – 50% |
| Vincamine | $10^{-6}$ | – 5% | + 6% | + 3% | 0% |
| Piribedil | $10^{-6}$ | – 4% | + 9% | – 2% | + 4% |
| Pentoxyfyllin | $10^{-6}$ | + 1% | – 5% | – 2% | + 3% |

I = (L)-1-diphenylmethyl-3-methyl-3-(3,4-ethylene-dioxybenzyl)-4-methylpiperazine
II = (L)-1-diphenylmethyl-3-methyl-3-(3,4-methylene-dioxybenzyl)-4-methylpiperazine
III = (L)-1-(p,p'-difluorophenylmethyl)-3-methyl-3-(3,4-methylenedioxybenzyl)-4-methylpiperazine
IV = (L)-1-(p-fluorophenyl-phenylmethyl)-3-methyl-3-(3,4-methylenedioxybenzyl)-4-methylpiperazine Under A in Table 1 is reported how strongly the test substance, in the dose indicated, inhibits the reduction in circulation in a perfused rabbit ear induced by histamine (1.5 × $10^{-6}$ M) or adrenalin (3 × $10^{-8}$ M) [method modified after: Aust. J. exp. Biol. med. Sci. 46, 739 (1968)]. Column B shows to what degree the contraction induced by a 5 × $10^{-4}$ M calcium chloride solution on a calcium-deprived and potassium-depolarized strip of blood vessel (rat aorta) is inhibited [method in imitation of: Brit. J. Pharmac. 36, 549 (1969)]. Under C, the corresponding values for serotonin antagonism are given, as measured in KrebsHenseleit solution on strips of blood vessel. The values indicate how strongly the contraction brought about by $10^{-6}$ M serotonin is inhibited by the test substance.

The new compounds further possess a good anti-arrhythmic efficacy which can be demonstrated by determination of the functional refractory time in the isolated left guinea-pig auricle using the method of Govier [cf. J. Pharm. Exp. Ther. 148, 100 (1965)].

Table 2 shows the data so obtained. RP signifies the increase in the refractory time in percent.

TABLE 2

| Substance | Dose (M) | RP |
|---|---|---|
| I | $10^{-5}$ | 47 |
| II | $10^{-5}$ | 49 |
| III | $10^{-5}$ | 28 |
| IV | $10^{-5}$ | 55 |
| Vincamine | $10^{-5}$ | 21 |
| Piribedil | $10^{-5}$ | 4 |
| Pentoxyfyllin | $10^{-5}$ | 0 |

I – IV - See Table 1

The new compounds thus are well adaptable to the treatment of vascular diseases such as peripheral and cerebral circulatory disturbances. Further, because of the calcium-antagonistic properties and refractory time-lengthening properties, they can be used for the treatment of coronary cardiac diseases and the disturbances of the cardiac rhythm which are associated therewith.

The new compounds and their salts are to be orally and parenterally administered. The daily dose is about 0.1 – 3.0 mg/kg for intravenous or intramuscular administration and between about 0.5 – 10 mg/kg for oral administration. For administration, the known galenic dosage unit forms such as tablets, dragees, capsules, and solutions are suitable.

A better understanding of the present invention and of its many advantages will be had by referring to the following specific examples, given by way of illustration. Examples A-G pertain to the preparation of starting materials.

EXAMPLE A

By the reaction of 3,4-dihydroxyphenyl-α-alanine methyl ester with benzyl bromide in methyl-ethyl ketone under reflux, N-benzyl-3,4-(dibenzyloxyphenyl)-α-alanine methyl ester is obtained (m.p.$_{HCl}$ = 170° C.), which forms N-benzyl-N-cyanomethyl-3,4-dibenzyloxyphenyl-α-alanine methyl ester (m.p. = 107° C.) in the cold with aqueous formaldehyde solution and potassium cyanide. From this compound, 3-methyl-3-(3,4-dibenzyloxyphenyl)-4-benzylpiperazinone-(2) (m.p. = 155° C) is obtained by hydrogenation with H$_2$/Raney nickel under pressure, from which 3-methyl-3-(3,4-dihydroxybenzyl)-4-benzylpiperazinone-(2)-hydrobromide (m.p. = 161° – 163° C.) is obtained with concentrated hydrobromic acid at room temperature. If this compound is reacted with 1,2-dichloroethane and potassium carbonate in the presence of copper powder in dimethylsulfoxide, 3-methyl-3-(3,4-ethylenedioxybenzyl)-4-benzylpiperazinone-(2) (Aa) is obtained. m.p. = 196° C.

In an analogous fashion are obtained:
(AaD) (D)-3-methyl-3-(3,4-ethylenedioxybenzyl)-4-benzylpiperazinone-(2), after extraction with chloroform
 m.p. = 114° C. (isopropanol)
 $[\alpha]_D^{20}$ = – 33.6° (c = 1, methanol)
(AaL) (L)-3-methyl-(3,4-ethylenedioxybenzyl)-4-benzylpiperazinone-(2), after extraction with chloroform
 m.p. = 115° C. (isopropanol)

$[\alpha]_D^{20} = + 34°$ (c = 1, methanol)
(Ab) 3-methyl-3-(3,4-methylenedioxybenzyl)-4-benzyl-piperazinone-(2)
   m.p. = 167° - 169° C. (isopropanol)
(AbD) (D)-3-methyl-3-(3,4-methylenedioxybenzyl)-4-benzylpiperazinone-(2), after extraction with chloroform
   m.p. = 133° - 135° C. (isopropanol)
   $[\alpha]_D^{20} = - 44°$ (c = 1, methanol)
(AbL) (L)-3-methyl-3-(3,4-methylenedioxybenzyl)-4-benzylpiperazinone-(2), after extraction with chloroform
   m.p. = 133° - 135° C. (isopropanol)
   $[\alpha]_D^{20} = + 44.1°$ (c = 1, methanol)

EXAMPLE B

From the compounds obtained according to A, the following compounds can be prepared by hydrogenation in the presence of palladium as a catalyst in glacial acetic acid:
(Ba) 3-methyl-3-(3,4-methylenedioxybenzyl)-piperazinone-(2)
   m.p. = 139° - 141° C. (isopropanol)
(BaD) (D)-3-methyl-3-(3,4-methylenedioxybenzyl)-piperazinone-(2)
   m.p. = 81° - 83° C. (methanol)
   $[\alpha]_D^{20} = + 27.8°$ (c = 1, methanol)
(BaL) (L)-3-methyl-3-(3,4-methylenedioxybenzyl)-piperazinone-(2)
   m.p. = 81° - 83° C. (methanol)
   $[\alpha]_D^{20} = - 28°$ (c = 1, methanol)
(Bb) 3-methyl-3-(3,4-ethylenedioxybenzyl)-piperazinone-(2)
   m.p. = 125° C. (diisopropylether)
(BbD) (D)-3-methyl-3-(3,4-ethylenedioxybenzyl)-piperazinone-(2)
   m.p. = 112° - 114° C. (diethylether)
   $[\alpha]_D^{20} = + 41.2°$ (c = 1, methanol)
(BbL) (L)-3-methyl-3-(3,4-ethylenedioxybenzyl)-piperazinone-(2)
   m.p. = 112° - 114° C. (diethylether)
   $[\alpha]_D^{20} = - 41.4°$ (c = 1, methanol)

EXAMPLE C

By alkylation with alkyl iodide in acetone and in the presence of potassium carbonate, the corresponding 4-alkyl derivatives are obtained from the compounds given in B.
(Ca) 3-methyl-3-(3,4-methylenedioxybenzyl)-4-methylpiperazinone-(2)
   m.p. = 134° - 136° C. (isopropanol)
(CaD) (D)-3-methyl-3-(3,4-methylenedioxybenzyl)-4-methylpiperazinone-(2)
   m.p.$_{HCl}$ = 224° C. (isopropanol)
   $[\alpha]_D^{20} = + 15.5°$ (c = 1, methanol)
(CaL) (L)-3-methyl-3-(3,4-methylenedioxybenzyl)-4-methylpiperazinone-(2)
   m.p.$_{HCl}$ = 222° C. (isopropanol)
   $[\alpha]_D^{20} = - 15.8°$ (c = 1, methanol)
(Cb) 3-methyl-3-(3,4-ethylenedioxybenzyl)-4-methylpiperazinone-(2)
   m.p. = 144° C. (diisopropylether)
(CbD) (D)-3-methyl-3-(3,4-ethylenedioxybenzyl)-4-methylpiperazinone-(2)
   m.p. = 101° C. (diisopropylether)
   $[\alpha]_D^{20} = + 48.5°$ (c = 1, methanol)
(CbL) (L)-3-methyl-3-(3,4-ethylenedioxybenzyl)-4-methylpiperazinone-(2)
   m.p. = 100° C. (diisopropylether)
   $[\alpha]_D^{20} = - 48.0°$ (c = 1, methanol)

EXAMPLE D

By reaction with acyl halides, the corresponding 4-acyl compounds are obtained from the 3,4-alkylenedioxybenzyl derivatives of 3-methylpiperazinone-(2), which acyl compounds can be converted by treatment with sodium hydride in dimethylformamide and, thereafter, by treatment with optionally halosubstituted diphenylmethyl bromide, into the corresponding 1-diphenylmethyl-3-methyl-3-(3,4-alkylenedioxybenzyl)-4-acylpiperazinone-(2) compounds. These can be used further without purification.

EXAMPLE E

By the reaction of 3-methyl-3-(3,4-ethylenedioxybenzyl)-4-methylpiperazinone-(2) (Cb) with sodium hydride in dimethylformamide and the addition of p-fluorophenyl-phenylmethyl chloride, 1-(p-fluorophenyl-phenylmethyl)-3-methyl-3-(3,4-ethylenedioxybenzyl)-4-methylpiperazinone-(2) (Ea) is obtained. m.p. = 130° C. (diisopropylether).

EXAMPLE F

By the reaction of 3-methyl-3-(3,4-ethylenedioxybenzyl)-piperazinone-(2) (Bb) with sodium hydride in dimethylformamide and subsequent reaction with diphenylmethyl bromide, 1-diphenylmethyl-3-methyl-3-(3,4-ethylenedioxybenzyl)-piperazinone-(2) (Fa) is obtained.

EXAMPLE G (D)-3-methyl-3-(3,4-dibenzyloxybenzyl)-4-benzyl-piperazinone-(2) is obtained from (D)-3-methyl-3-(3,4-dihydroxybenzyl)-4-benzylpiperazinone-(2) (cf. A) by reaction with benzyl bromide in acetone and in the presence of potassium carbonate. If the first-mentioned compound is reacted with sodium hydride and subsequently with diphenylmethyl bromide in dimethylformamide, (D)-1-diphenylmethyl-3-methyl-3-(3,4-dibenzyloxybenzyl)-4-benzylpiperazinone-(2) is formed, from which the benzyl groups can be cleaved by hydrogenation with palladium/hydrogen. From the dihydroxybenzyl compound so obtained, (D)-1-diphenylmethyl-3-methyl-3-(3,4-diacetoxybenzyl)-piperazinone-(2) is obtained by reaction with acetyl chloride in glacial acetic acid/HCl. If this compound is treated with methyl iodide and subsequently with lithium aluminum hydride, (D)-1-diphenylmethyl-3-methyl-3-(3,4-dihydroxybenzyl)-4-methylpiperazine (Ga) is formed,
   m.p.$_{HCl}$ = 176° - 178° C. (ethanol)
   $[\alpha]_{334\,NM}^{20} = + 11.2°$ In the same fashion, one obtains the corresponding (L)-compound
   m.p.$_{HCl}$ = 175° - 177° C. (ethanol)
   $[\alpha]_{334\,NM}^{20} = - 11.2°$

EXAMPLE 1

20.8 g of 3-methyl-3-(3,4-ethylenedioxybenzyl)-4-benzylpiperazinone-(2) (Aa) are suspended in 150 ml of dry tetrahydrofuran and added dropwise with stirring over the course of an hour into a boiling suspension of 6.8 g of lithium aluminum hydride in 400 ml of tetrahydrofuran. The mixture is held at boiling for a further five hours. After the careful addition of water, the mixture is filtered and the filtrate is evaporated. 18.2 g (91.5%) of 3-methyl-3-(3,4-ethylenedioxybenzyl)-4-benzylpiperazine are obtained as an oily residue which, after lengthy standing, crystallizes (m.p. = 128° – 130° C.)

18 g of this compound are dissolved in 150 ml of glacial acetic acid, combined with 2 g of 10% palladium black, and hydrogenated at room temperature. The catalyst is removed by filtration and the filtrate is evaporated to dryness in vacuum. The residue is taken up in 150 ml of chloroform and made strongly alkaline with 20% ammonium hydroxide solution. The organic phase is extracted three times with 40 ml portions of water and the solvent is distilled off in vacuum. The residue is taken up into toluene and the solution is again reduced to dryness in order to remove the water azeotropically. The remaining oil is distilled in high vacuum. 11.6 g (88.2%) of 3-methyl-3-(3,4-ethylenedioxybenzyl)-piperazine (1a) are obtained.
 b.p. = 156° – 158° C./0.01 mm Hg.

In the same fashion are obtained:
(1aD) (D)-3-methyl-3-(3,4-ethylenedioxybenzyl)-piperazine
 b.p. = 158°– 160° C./0.02 mm Hg.
 $[\alpha]_D^{20} = + 12.6°$ (c = 1, methanol)
(1aL) (L)-3-methyl-3-(3,4-ethylenedioxybenzyl)-piperazine
 b.p. = 171° – 173° C./0.1 mm Hg.
 $[\alpha]_D^{20} = - 12.6°$ (c = 1, methanol)
(1b) 3-methyl-3-(3,4-methylenedioxybenzyl)-piperazine
 b.p. = 128° – 130° C./0.005 mm Hg.
(1bD) (D)-3-methyl-3-(3,4-methylenedioxybenzyl)-piperazine
 b.p. = 148° – 151° C/0.05 mm Hg.
 $[\alpha]_D^{20} = + 15.5°$ (c = 1, methanol)
(1bL) (L)-3-methyl-3-(3,4-methylenedioxybenzyl)-piperazine
 b.p. = 153° – 155° C./0.05 mm Hg.
 $[\alpha]_D^{20} = - 15.3°$ (c = 1, methanol)

EXAMPLE 2

A solution of 14 g of 3-methyl-3-(3,4-methylenedioxybenzyl)-4-methylpiperazinone-(2) (Ca) in 50 ml of tetrahydrofuran is added dropwise with stirring over the course of an hour into a boiling suspension of 6 g of lithium aluminum hydride in 200 ml of dry tetrahydrofuran. The mixture is held for a further three hours at the boiling point. After careful addition of water and filtration, the solution is evaporated to dryness in vacuum. The remaining oil is distilled in high vacuum. 11.3 g (85.6%) of 3-methyl-3-(3,4-methylenedioxybenzyl)-4-methylpiperazine (2a) are obtained.
 b.p. = 143° – 145° C./0.01 mm Hg.
 m.p. = 79° C.

In the same fashion are obtained:
(2aD) (D)-3-methyl-3-(3,4-methylenedioxybenzyl)-4-methylpiperazine
 b.p. = 148° – 150° C./0.01 mm Hg.
 $[\alpha]_D^{20} = - 20.3°$ (c = 1, methanol)
(2aL) (L)-3-methyl-3-(3,4-methylenedioxybenzyl)-4-methylpiperazine
 b.p. = 148°– 150° C./0.01 mm Hg.
 $[\alpha]_D^{20} = + 20.5°$ (c = 1, methanol)
(2b) 3-methyl-3-(3,4-ethylenedioxybenzyl)-4-methylpiperazine
 b.p. = 180° C./0.01 mm Hg.
(2bD) (D)-3-methyl-3-(3,4-ethylenedioxybenzyl)-4-methylpiperazine
 b.p. = 163° – 166° C./0.01 mm Hg.
 $[\alpha]_D^{20} = - 22.6°$ (c = 1, methanol)
(2aL) (L)-3-methyl-3-(3,4-ethylenedioxybenzyl)-4-methylpiperazine
 b.p. = 163° – 166° C./0.01 mm Hg.
 $[\alpha]_D^{20} = + 22.8°$ (c = 1, methanol)

EXAMPLE 3

12.4 g of 3-methyl-3-(3,4-ethylenedioxybenzyl)-piperazine (1a) are dissolved in 200 ml of dry acetone, combined with 20.7 g of potassium carbonate and 14.8 g of diphenylmethyl bromide, and heated for four hours with stirring under reflux. The inorganic salts are filtered off and the filtrate is evaporated to dryness is vacuum. The residue is taken up in 300 ml of diethyl ether and washed with water until the wash water no longer contains halogen. After drying with magnesium sulfate, hydrogen chloride is introduced into the organic phase. The precipitated hydrochloric is filtered off and washed with a little ether. Thereafter, it it suspended in a little water, combined with 20% ammonium hydroxide solution until alkaline, and extracted three times with 50 ml of diethyl ether. The organic phases are dried over magnesium sulfate and reduced to dryness. 19 g (91.6%) of 1-diphenylmethyl-3-methyl-3-(3,4-ethylenedioxybenzyl)-piperazine (3a) are obtained.
 m.p. = 144° C. (diisopropylether)

In an analogous fashion are obtained:
(3aD) (D)-1-(diphenylmethyl)-3-methyl-3-(3,4-ethylenedioxybenzyl)-piperazine, as a glassy solidified resin
 $[\alpha]_D^{20} = + 20.0°$ (c = 1, methanol)
(3aL) (L)-1-(diphenylmethyl)-3-methyl-3-(3,4-ethylenedioxybenzyl)-piperazine, as a glassy solidified resin
 $[\alpha]_D^{20} = - 20°$ (c = 1, methanol)
(3b) 1-(p-chlorophenyl-phenylmethyl)-3-methyl-3-(3,4-ethylenedioxybenzyl)-piperazine-dihydrochloride
 m.p. = 179° – 181° C. (acetone)
(3bD) (D)-1-(p-chlorophenyl-phenylmethyl)-3-methyl-3-(3,4-ethylenedioxybenzyl)-piperazine, as a glassy solidified resin
 $[\alpha]_D^{20} = + 16.3°$ (c = 1, methanol)
(3bL) (L)-1-(p-chlorophenyl-phenylmethyl)-3-methyl-3-(3,4-ethylenedioxybenzyl)-piperazine as a glassy solidified resin
 $[\alpha]_D^{20} = - 16.6°$ (c = 1, methanol)
(3cD) (D)-1-(p,p'-dichlorodiphenylmethyl)-3-methyl-3-(3,4-ethylenedioxybenzyl)-piperazine, as a glassy solidified resin
 $[\alpha]_D^{20} = + 14.3°$ (c = 1, methanol)
(3cL) (L)-1-(p,p'-dichlorodiphenylmethyl)-3-methyl-3-(3,4-ethylenedioxybenzyl)-piperazine, as a glassy solidified resin
 $[\alpha]_D^{20} = - 14.5°$ (c = 1, methanol)
(3dD) (D)-1-(p-fluorophenyl-phenylmethyl)-3-methyl-3-(3,4-ethylenedioxybenzyl)-piperazine, as a glassy solidified resin
 $[\alpha]_D^{20} = + 17.5°$ (c = 1, methanol)
(3dL) (L)-1-(p-fluorophenyl-phenylmethyl)-3-methyl-3-(3,4-ethylenedioxybenzyl)-piperazine, as a glassy solidified resin
 $[\alpha]_D^{20} = - 17.1°$ (c = 1, methanol)
(3e) 1-(p,p'-difluorodiphenylmethyl)-3-methyl-3-(3,4-ethylenedioxybenzyl)-piperazine-dihydrochloride
 m.p. = 191° – 193° C. (isopropanol)
(3eD) (D)-1-(p,p'-difluorodiphenylmethyl)-3-methyl-3-(3,4-ethylenedioxybenzyl)-piperazine, as a glassy solidified resin
 $[\alpha]_D^{20} = + 16.8°$ (c = 1, methanol)

(3eL) (L)-1-(p,p'-difluoridiphenylmethyl)-3-methyl-3-(3,4-ethylenedioxybenzyl)-piperazine, as a glassy solidified resin
$[\alpha]_D^{20} = -17.0°$ (c = 1, methanol)

(3f) 1-diphenylmethyl-3-methyl-3-(3,4-methylenedioxybenzyl)-piperazine-dihydrochloride
m.p. = 170° C. (isopropanol)

(3fD) (D)-1-diphenylmethyl-3-methyl-3-(3,4-methylenedioxybenzyl)-piperazine, as a glassy solidified resin
$[\alpha]_D^{20} = + 15.6°$ (c = 1, methanol)

(3fL) (L)-1-diphenylmethyl-3-methyl-3-(3,4-methylenedioxybenzyl)-piperazine, as a glassy solidified resin
$[\alpha]_D^{20} = - 15.3°$ (c = 1, methanol)

(3g) 1-(p-chlorophenyl-phenylmethyl)-3-methyl-3-(3,4-methylenedioxybenzyl)-piperazine-dihydrochloride
m.p. = 174° C. (isopropanol)

(3gD) (D)-1-(p-chlorophenyl-phenylmethyl)-3-methyl-3-(3,4-methylenedioxybenzyl)-piperazine, as a glassy solidified resin
$[\alpha]_D^{20} = + 11.8°$ (c = 1, methanol)

(3gL) (L)-1-(p-chlorophenyl-phenylmethyl)-3-methyl-3-(3,4-methylenedioxybenzyl)-piperazine, as a glassy solidified resin
$[\alpha]_D^{20} = - 12.0°$ (c = 1, methanol)

(3hD) (D)-1-(p,p'-dichlorodiphenylmethyl)-3-methyl-3-(3,4-methylenedioxybenzyl)-piperazine, as a glassy solidified resin
$[\alpha]_D^{20} = + 8.6°$ (c = 1, methanol)

(3hL) (L)-1-(p,p'-dichlorodiphenylmethyl)-3-methyl-3-(3,4-methylenedioxybenzyl)-piperazine, as a glassy solidified resin
$[\alpha]_D^{20} = - 8.8°$ (c = 1, methanol)

(3iD) (D)-1-(p-fluorophenyl-phenylmethyl)-3-methyl-3-(3,4-methylenedioxybenzyl)-piperazine, as a glassy solidified resin
$[\alpha]_D^{20} = + 13.4°$ (c = 1, methanol)

(3iL) (L)-1-(p-fluorophenyl-phenylmethyl)-3-methyl-3-(3,4-methylenedioxybenzyl)-piperazine, as a glassy solidified resin
$[\alpha]_D^{20} = - 13.5°$ (c = 1, methanol)

(3j) 1-(p,p'-difluorodiphenylmethyl)-3-methyl-3-(3,4-methylenedioxybenzyl)-piperazine-hydrochloride
m.p. = 174° C. (isopropanol)

(3jD) (D)-1-(p,p'-difluorodiphenylmethyl)-3-methyl-3-(3,4-methylenedioxybenzyl)-piperazine, as a glassy solidified resin
$[\alpha]_D^{20} = + 12.0°$ (c = 1, methanol)

(3jL) (L)-1-(p,p'-difluorodiphenylmethyl)-3-methyl-3-(3,4-methylenedioxybenzyl)-piperazine, as a glassy solidified resin
$[\alpha]_D^{20} = - 12.2°$ (c = 1, methanol)

EXAMPLE 4

15 g of 1-diphenylmethyl-3-methyl-3-(3,4-ethylenedioxybenzyl)-piperazine (3a) are dissolved in 200 ml of acetone, combined with 10 g of potassium carbonate, and heated to boiling with stirring. 5.6 g of methyl iodide in 50 ml of acetone are added dropwise in the course of two hours. After a further five hours at reflux with stirring, the mixture is filtered and the filtrate evaporated to dryness in vacuum. The residue is taken up in 200 ml of diethyl ether, washed free of halogen with water, dried over sodium sulfate, and the filtrate is evaporated to dryness in vacuum. 12.9 g (83%) of 1-diphenylmethyl-3-methyl-3-(3,4-ethylenedioxybenzyl)-4-methylpiperazine (4a) are obtained.

m.p. = 118° - 120° C. (diisopropylether)

In an analogous fashion are obtained:

(4aD) (D)-1-diphenylmethyl-3-methyl-3-(3,4-ethylenedioxybenzyl)-4-methylpiperazine, as a glassy solidified resin
$[\alpha]_D^{20} = - 15.7°$ (c = 1, methanol)

(4aL) (L)-1-diphenylmethyl-3-methyl-3-(3,4-ethylenedioxybenzyl)-4-methylpiperazine, as a glassy solidified resin
$[\alpha]_D^{20} = + 15.8°$ (c = 1, methanol)

(4bD) (D)-1-diphenylmethyl-3-methyl-3-(3,4-ethylenedioxybenzyl)-4-ethylpiperazine, as a glassy solidified resin
$[\alpha]_D^{20} = - 9.1°$ (c = 1, methanol)

(4bL) (L)-1-diphenylmethyl-3-methyl-3-(3,4-ethylenedioxybenzyl)-4-ethylpiperazine, as a glassy solidified resin
$[\alpha]_D^{20} = + 9.2°$ (c = 1, methanol)

(4cD) (D)-1-diphenylmethyl-3-methyl-3-(3,4-ethylenedioxybenzyl)-4-n-propylpiperazine, as a glassy solidified resin
$[\alpha]_D^{20} = - 5.3°$ (c = 1, methanol)

(4cL) (L)-1-diphenylmethyl-3-methyl-3-(3,4-ethylenedioxybenzyl)-4-n-propylpiperazine, as a glassy solidified resin
$[\alpha]_D^{20} = + 5.4°$ (c = 1, methanol)

(4d) 1-(p-chlorophenyl-phenylmethyl)-3-methyl-3-(3,4-ethylenedioxybenzyl)-4-methylpiperazine-dihydrochloride
m.p. = 223° - 225° C. (ethanol)

(4dD) (D)-1-(p-chlorophenyl-phenylmethyl)-3-methyl-3-(3,4-ethylenedioxybenzyl)-4-methylpiperazine, as a glassy solidified resin
$[\alpha]_D^{20} = - 15.7°$ (c = 1, methanol)

(4dL) (L)-1-(p-chlorophenyl-phenylmethyl)-3-methyl-3-(3,4-ethylenedioxybenzyl)-4-methylpiperazine, as a glassy solidified resin
$[\alpha]_D^{20} = + 15.5°$ (c = 1, methanol)

(4eD) (D)-1-(p,p'-dichlorodiphenylmethyl)-3-methyl-3-(3,4-ethylenedioxybenzyl)-4-methylpiperazine, as a glassy solidified resin
$[\alpha]_D^{20} = - 15.1°$ (c = 1, methanol)

(4eL) (L)-1-(p,p'-dichlorodiphenylmethyl)-3-methyl-3-(3,4-ethylenedioxybenzyl)-4-methylpiperazine, as a glassy solidified resin
$[\alpha]_D^{20} = + 15.3°$ (c = 1, methanol)

(4f) 1-(p-fluorophenyl-phenylmethyl)-3-methyl-3-(3,4-ethylenedioxybenzyl)-4-methylpiperazine
m.p. = 189° - 191° C. (ethanol)

(4fD) (D)-1(p-fluorophenyl-phenylmethyl)-3-methyl-3-(3,4-ethylenedioxybenzyl)-4-methylpiperazine, as a glassy solidified resin
$[\alpha]_D^{20} = - 14.0°$ (c = 1, methanol)

(4fL) (L)-1-(p-fluorophenyl-phenylmethyl)-3-methyl-3-(3,4-ethylenedioxybenzyl)-4-methylpiperazine, as a glassy solidified resin
$[\alpha]_D^{20} = + 14.1°$ (c = 1, methanol)

(4g) 1-(p,p'-difluorodiphenylmethyl)-3-methyl-3-(3,4-ethylenedioxybenzyl)-4-methylpiperazine-dihydrochloride
m.p. = 224° - 226° C. (methanol)

(4gD) (D)-1-(p,p'-difluorodiphenylmethyl)-3-methyl-3-(3,4-ethylenedioxybenzyl)-4-methylpiperazine, as a glassy solidified resin
$[\alpha]_D^{20} = - 13.6°$ (c = 1, methanol)

(4gL) (L)-1-(p,p'-difluorodiphenylmethyl)-3-methyl-3-(3,4-ethylenedioxybenzyl)-4-methylpiperazine, as a glassy solidified resin (4h) 1-diphenylmethyl-3-methyl-3-(3,4-methylenedioxybenzyl)-4-methylpiperazine-dihydrochloride, as a hydrate
m.p. = 195° - 198° C. (ethanol)
$[\alpha]_D^{20} = + 13.5°$ (c = 1, methanol)

(4hD) (D)-1-diphenylmethyl-3-methyl-3-(3,4-methylenedioxybenzyl)-4-methylpiperazine, as a glassy solidified resin
$[\alpha]_D^{20} = - 20.0°$ (c = 1, methanol)

(4hL) (L)-1-diphenylmethyl-3-methyl-3-(3,4-methylenedioxybenzyl)-4-methylpiperazine, as a glassy solidified resin
$[\alpha]_D^{20} = + 19.8°$ (c = 1, methanol)

(4iD) (D)-1-diphenylmethyl-3-methyl-3-(3,4-methylenedioxybenzyl)-4-ethylpiperazine, as a glassy solidified resin
$[\alpha]_D^{20} = - 12.4°$ (c = 1, methanol)

(4iL) (L)-1-diphenylmethyl-3-methyl-3-(3,4-methylenedioxybenzyl)-4-ethylpiperazine
$[\alpha]_D^{20} = + 12.2°$ (c = 1, methanol)

(4jD) (D)-1-diphenylmethyl-3-methyl-3-(3,4-methylenedioxybenzyl)-4-n-propylpiperazine
$[\alpha]_D^{20} = - 8.1°$ (c = 1, methanol)

(4jL) (L)-1-diphenylmethyl-3-methyl-3-(3,4-methylenedioxybenzyl)-4-n-propylpiperazine
$[\alpha]_D^{20} = + 8.0°$ (c = 1, methanol)

(4k) 1-(p-chlorophenyl-phenylmethyl)-3-methyl-3-(3,4-methylenedioxybenzyl)-4-methylpiperazine-dihydrochloride
m.p. = 193° C. (isopropanol)

(4kD) (D)-1-(p-chlorophenyl-phenylmethyl)-3-methyl-3-(3,4-methylenedioxybenzyl)-4-methylpiperazine, as a glassy solidifed resin
$[\alpha]_D^{20} = - 21.0°$ (c = 1, methanol)

(4kL) (L)-1-(p-chlorophenyl-phenylmethyl)-3-methyl-3-(3,4-methylenedioxybenzyl)-4-methylpiperazine, as a glassy solidifed resin
$[\alpha]_D^{20} = + 20.8$ (c = 1, methanol)

(4lD) (D)-1-(p,p'-dichlorodiphenylmethyl)-3-methyl-3-(3,4-methylenedioxybenzyl)-4-methylpiperazine, as a glassy solidifed resin
$[\alpha]_D^{20} = - 19.3°$ (c = 1, methanol)

(4lL) (L)-1-(p,p'-dichlorodiphenylmethyl)-3-methyl-3-(3,4-methylenedioxybenzyl)-4-methylpiperazine, as a glassy solidified resin
$[\alpha]_D^{20} = + 19.5°$ (c = 1, methanol)

(4mD) (D)-1-(p-fluorophenyl-phenylmethyl)-3-methyl-3-(3,4-methylenedioxybenzyl)-4-methylpiperazine, as a glassy solidifed resin
$[\alpha]_D^{20} = - 22.4°$ (c = 1, methanol)

(4mL) (L)-1-(p-fluorophenyl-phenylmethyl)-3-methyl-3-(3,4-methylenedioxybenzyl)-4-methylpiperazine, as a glassy solidifed resin
$[\alpha]_D^{20} = + 22.5°$ (c = 1, methanol)

(4n) 1-(p,p'-difluorophenylmethyl)-3-methyl-3-(3,4-methylenedioxybenzyl)-4-methylpiperazine-dihydrochloride, as a hydrate
m.p. = 201° C. (isopropanol)

(4nD) (D)-1-(p,p'-difluorophenylmethyl)-3-methyl-3-(3,4-methylenedioxybenzyl)-4-methylpiperazine, as a glassy solidified resin
$[\alpha]_D^{20} = - 20.4°$ (c = 1, methanol)

(4nL) (L)-1-(p,p'-difluorophenylmethyl)-3-methyl-3-(3,4-methylenedioxybenzyl)-4-methylpiperazine, as a glassy solidified resin
$[\alpha]_D^{20} = + 20.6°$ (c = 1, methanol)

EXAMPLE 5

19 g of 3-methyl-3-(3,4-ethylenedioxybenzyl)-piperazinone-(2) (Bb) are dissolved in 120 ml of benzene and combined with 8.1 g of triethylamine. At room temperature, with stirring, 8.7 g of chloroformic acid ethyl ester in 30 ml of benzene are added dropwise. After 12 hours, the reaction batch is washed free of halogen with water and the organic phase is evaporated to dryness. 21 g of 3-methyl-3-(3,4-ethylenedioxybenzyl)-4-carbethoxypiperazinone-(2) (m.p. = 122° - 124° C.) (isopropanol) are obtained, which are dissolved in 100 ml of tetrahydrofuran and added dropwise with stirring to a boiling suspension of 8 g of lithium aluminum hydride in 200 ml of tetrahydrofuran. After four hours, the compound is carefully decomposed with water, filtered, and the filtrate is evaporated to dryness in vacuum. After distillation in high vacuum, 14.3 g (87%) of 3-methyl-3-(3,4-ethylenedioxybenzyl)-4-methylpiperazine (2b) are obtained.
b.p. = 180° C./0.01 mm Hg.

In the same fashion, the compounds described in Example 2 are obtained.

EXAMPLE 6

6.2 g of 3-methyl-3-(3,4-methylenedioxybenzyl)-4-methylpiperazine (2a) are reacted as in Example 3 with 7 g of diphenylmethyl bromide. The reaction mixture is filtered, the filtrate reduced to dryness and dissolved in diethyl ether. On introducing hydrogen chloride, 11 g (90%) of 1-diphenylmethyl-3-methyl-3-(3,4-methylenedioxybenzyl)-4-methylpiperazine-dihydrochloride (4h) are precipitated.
m.p. = 196° - 198° C. (ethanol)

In an analogous fashion, the remaining compounds of Example 4 are obtained.

EXAMPLE 7

13.5 g of 1-diphenylmethyl-3-methyl-3-(3,4-ethylenedioxybenzyl)-4-carbethoxypiperazinone-(2) (cf. D) are dissolved in 90 ml of tetrahydrofuran and added dropwise to a boiling suspension of 4.1 g of lithium aluminum hydride in 200 ml of tetrahydrofuran. After 3 hours, the residue is decomposed with water, filtered, and evaporated to dryness in vacuum. 9.8 g (85%) of 1-diphenylmethyl-3-methyl-3-(3,4-ethylenedioxybenzyl)-4-methylpiperazine (4a) are obtained.
m.p. = 120° C. (diisopropylether)

In an analogous fashion, the other compounds mentioned in Example 4 are obtained.

EXAMPLE 8

3.1 g of 1-(p-fluorophenyl-phenylmethyl)-3-methyl-3-(3,4-ethylenedioxybenzyl)-4-methylpiperazinone-(2) (Da) are dissolved in 15 ml of tetrahydrofuran and, with stirring, are added dropwise over 30 minutes to a boiling suspension of 0.8 g of lithium aluminum hydride in 100 ml of tetrahydrofuran. After 3 hours, the batch is carefully combined with water, filtered, and the solvent distilled off in vacuum. 2.7 g (90%) of 1-(p-fluorophenyl-phenylmethyl)-3-methyl-3-(3,4-ethylenedioxybenzyl)-4-methylpiperazine (4f) are obtained.
m.p.$_{HCl}$ = 189° - 191° C. (ethanol)

In the same fashion, the compounds mentioned in Example 3 are obtained.

EXAMPLE 9

12.4 g of 1-diphenylmethyl-3-methyl-3-(3,4-ethylenedioxybenzyl)-piperazine (3a) are dissolved in 100 ml of dry benzene and combined with 3.3 g of triethylamine. 3.6 g of chloroformic acid ethyl ester in 20 ml of benzene are added dropwise with stirring at room temperature. After 12 hours the solution is washed free of halogen with water and evaporated to dryness in vacuum. 13.1 g (90%) of 1-diphenylmethyl-3-methyl-3-(3,4-ethylenedioxybenzyl)-4-carbethoxypiperazine are obtained (m.p. = 153° - 155° C., diisopropylether), which are dissolved in 100 ml of dry tetrahydrofuran and added dropwise with stirring over 30 minutes to a boiling suspension of 3.8 g of lithium aluminum hydride in 200 ml of tetrahydrofuran. After three hours, the mixture is combined with water and filtered. The filtrate is evaporated to dryness in vacuum. 10.7 g (93%) of 1-diphenylmethyl-3-methyl-3-(3,4-ethylenedioxybenzyl)-4-methylpiperazine are obtained.

m.p. = 118° - 120° C. (diisopropylether)

In an analogous fashion, the remaining products mentioned in Example 4 are obtained.

EXAMPLE 10

6.5 g of 1-diphenylmethyl-3-methyl-3-(3,4-ethylenedioxybenzyl)-piperazinone-(2) (Fa) are dissolved in 30 ml of tetrahydrofuran and added dropwise with stirring into a boiling suspension of 2 g of lithium aluminum hydride in 100 ml of tetrahydrofuran. After three hours, water is carefully added, the mixture is filtered, and the filtrate reduced to dryness in vacuum. 5.6 g (89%) of 1-diphenylmethyl-3-methyl-3-(3,4-ethylenedioxybenzyl)-piperazine (3a) are obtained.

m.p. = 143° C. (diisopropylether)

In an analogous fashion, the compounds mentioned in Example 3 are obtained.

EXAMPLE 11

9.5 g of (D)-1-diphenylmethyl-3-methyl-3-(3,4-dihydroxybenzyl)-4-methylpiperazine-dihydrochloride (Ga) are suspended under nitrogen in 100 ml of toluene-tetrahydrofuran (1:1) and combined with 0.1 g of tributylbenzyl ammonium bromide and 11 g of 50% sodium hydroxide. The mixture is stirred for 20 minutes. Subsequently, 4.5 g of dibromethane in 20 ml of toluene-tetrahydrofuran (1:1) are added dropwise over 10 minutes. After 20 hours of stirring at 45° C., again 4.5 g of dibromethane are added. After a further 60 hours, the reaction solution is reduced in volume, taken up in 100 ml of toluene, washed free of halogen with water, dried, and evaporated to dryness in vacuum. The residue is taken up in 75 ml of diisopropylether, filtered, and the filtrate is combined with isopropanolic hydrochloric acid. The precipitate formed is filtered and dried in vacuum at 40° C. 8.1 g (80.6%) of (D)-1-diphenylmethyl-3-methyl-3-(3,4-ethylenedioxybenzyl)-4-methylpiperazine-dihydrochloride (4aD) are obtained.

m.p. = 215° - 217° C. (isopropanol)

$[\alpha]_D^{20} = -15.6°$ (free base, c = 1, methanol)

Correspondingly, the L-enantiomer (4aL) is obtained, also as the dihydrochloride.

m.p. = 214° - 215° C.

$[\alpha]_D^{20} = +15.6°$ (c = 1, methanol)

The compounds mentioned in Example 4 are prepared in an analogous fashion.

EXAMPLE 12

Using a tablet press, tablets of the following composition are pressed in the usual fashion:
200 mg — (L)-1-diphenylmethyl-3-methyl-3-(3,4-methylenedioxybenzyl)-4-methylpiperazine
150 mg — corn starch
13.50 mg — gelatin
45 mg — milk sugar
22.5 mg — talc
2.25 mg — "Aerosil" (chemically pure silic acid in a submicroscopically fine subdivision)
6.75 mg — potato starch (as a 6% paste)

EXAMPLE 13

In the usual fashion, dragees of the following composition were prepared:
100 mg — (L)-1-(p-fluorophenyl-phenylmethyl)-3-methyl-3-(3,4-methylenedioxybenzyl)-4-methylpiperazine
170 mg — core mass
160 mg — sugaring mass The core mass comprises 9 parts of corn starch, 3 parts of milk sugar, and 1 part of "Luviskol VA 64" (vinylpyrrolidonevinylacetate-copolymer 60 : 40, cf. Pharm. Ind. 1962, 586). The sugaring mass comprises 5 parts of cane sugar, 2 parts of corn starch, 2 parts of calcium carbonate, and 1 part of talc. The dragees so prepared are subsequently provided with a coating resistant to stomach juice.

EXAMPLE 14

50 g of (L)-1-diphenylmethyl-3-methyl-3-(3,4-ethylenedioxybenzyl)-4-methylpiperazine-diamidosulfonate are dissolved in 5 liters of water. The solution is adjusted to a pH of 3.5 with 0.1 N sodium acetate and made isotonic with sodium choride. Thereafter, the material was filled into ampules 2 ml of volume.

What is claimed is:

1. An alkylenedioxy piperazine compound of the formula

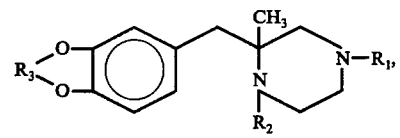

or a salt thereof with a physiologically tolerable acid, wherein
  $R_1$ is hydrogen, diphenylmethyl, or diphenylmethyl wherein one of the phenyl groups has a halogen substituent;
  $R_2$ is hydrogen, hydrocarbon having 1-5 carbon atoms, or such hydrocarbon substituted by amino or hydroxy; and
  $R_3$ is methylene or ethylene.

2. A compound as in claim 1 which is 3-methyl-3-(3,4-ethylenedioxybenzyl)-piperazine.

3. A compound as in claim 1 which is (D)-3-methyl-3-(3,4-ethylenedioxybenzyl)-piperazine.

4. A compound as in claim 1 which is (L)-3-methyl-3-(3,4-ethylenedioxybenzyl)-piperazine.

5. A compound as in claim 1 which is 3-methyl-3-(3,4-methylenedioxybenzyl)-piperazine.

6. A compound as in claim 1 which is (D)-3-methyl-3-(3,4-methylenedioxybenzyl)-piperazine.

7. A compound as in claim 1 which is (L)-3-methyl-3-(3,4-methylenedioxybenzyl)-piperazine.

8. A compound as in claim 1 which is 3-methyl-3-(3,4-methylenedioxybenzyl)-4-methylpiperazine.

9. A compound as in claim 1 which is (D)-3-methyl-3-(3,4-methylenedioxybenzyl)-4-methylpiperazine.

10. A compound as in claim 1 which is (L)-3-methyl-3-(3,4-methylenedioxybenzyl)-4-methylpiperazine.

11. A compound as in claim 1 which is 3-methyl-3-(3,4-ethylenedioxybenzyl)-4-methylpiperazine.

12. A compound as in claim 1 which is (D)-3-methyl-3-(3,4-ethylenedioxybenzyl)-4-methylpiperazine.

13. A compound as in claim 1 which is (L)-3-methyl-3-(3,4-ethylenedioxybenzyl)-4-methylpiperazine.

14. A compound as in claim 1 which is 1-diphenylmethyl-3-methyl-3-(3,4-ethylenedioxybenzyl)-piperazine.

15. A compound as in claim 1 which is (D)-1-(diphenylmethyl)-3-methyl-3-(3,4-ethylenedioxybenzyl)-piperazine.

16. A compound as in claim 1 which is (L)-1-(diphenylmethyl)-3-methyl-3-(3,4-ethylenedioxybenzyl)-piperazine.

17. A compound as in claim 1 which is 1-(p-chlorophenyl-phenylmethyl)-3-methyl-3-(3,4-ethylenedioxybenzyl)-piperazine.

18. A compound as in claim 1 which is (D)-1-(p-chlorophenyl-phenylmethyl)-3-methyl-3-(3,4-ethylenedioxybenzyl)-piperazine.

19. A compound as in claim 1 which is (L)-1-(p-chlorophenyl-phenylmethyl)-3-methyl-3-(3,4-ethylenedioxybenzyl)-piperazine.

20. A compound as in claim 1 which is (D)-1-(p,p'-dichlorodiphenylmethyl)-3-methyl-3-(3,4-ethylenedioxybenzyl)-piperazine.

21. A compound as in claim 1 which is (L)-1-(p,p'-dichlorodiphenylmethyl)-3-methyl-3-(3,4-ethylenedioxybenzyl)-piperazine.

22. A compound as in claim 1 which is (D)-1-(p-fluorophenyl-phenylmethyl)-3-methyl-3-(3,4-ethylenedioxybenzyl)-piperazine.

23. A compound as in claim 1 which is (L)-1-(p-fluorophenyl-phenylmethyl)-3-methyl-3-(3,4-ethylenedioxybenzyl)-piperazine.

24. A compound as in claim 1 which is 1-(p,p'-difluorodiphenylmethyl)-3-methyl-3-(3,4-ethylenedioxybenzyl)-piperazine.

25. A compound as in claim 1 which is (D)-1-(p,p'-difluorodiphenylmethyl)-3-methyl-3-(3,4-ethylenedioxybenzyl)-piperazine.

26. A compound as in claim 1 which is (L)-1-(p,p'-difluorodiphenylmethyl)-3-methyl-3-(3,4-ethylenedioxybenzyl)-piperazine.

27. A compound as in claim 1 which is 1-diphenylmethyl-3-methyl-3-(3,4-methylenedioxybenzyl)-piperazine.

28. A compound as in claim 1 which is (D)-1-diphenylmethyl-3-methyl-3-(3,4-methylenedioxybenzyl)-piperazine.

29. A compound as in claim 1 which is (L)-1-diphenylmethyl-3-methyl-3-(3,4-methylenedioxybenzyl)-piperazine.

30. A compound as in claim 1 which is 1-(p-chlorophenyl-phenylmethyl)-3-methyl-3-(3,4-methylenedioxybenzyl)-piperazine.

31. A compound as in claim 1 which is (D)-1-(p-chlorophenyl-phenylmethyl)-3-methyl-3-(3,4-methylenedioxybenzyl)-piperazine.

32. A compound as in claim 1 which is (L)-1-(p-chlorophenyl-phenylmethyl)-3-methyl-3-(3,4-methylenedioxybenzyl)-piperazine.

33. A compound as in claim 1 which is (D)-1-(p,p'-dichlorodiphenylmethyl)-3-methyl-3-(3,4-methylenedioxybenzyl)-piperazine.

34. A compound as in claim 1 which is (L)-1-(p,p'-dichlorodiphenylmethyl)-3-methyl-3-(3,4-methylenedioxybenzyl)-piperazine.

35. A compound as in claim 1 which is (D)-1-(p-fluorophenyl-phenylmethyl)-3-methyl-3-(3,4-methylenedioxybenzyl)-piperazine.

36. A compound as in claim 1 which is (L)-1-(p-fluorophenyl-phenylmethyl)-3-methyl-3-(3,4-methylenedioxybenzyl)-piperazine.

37. A compound as in claim 1 which is 1-(p,p'-difluorodiphenylmethyl)-3-methyl-3-(3,4-methylenedioxybenzyl)-piperazine.

38. A compound as in claim 1 which is (D)-1-(p,p'-difluorodiphenylmethyl)-3-methyl-3-(3,4-methylenedioxybenzyl)-piperazine.

39. A compound as in claim 1 which is (L)-1-(p,p'-difluorodiphenylmethyl)-3-methyl-3-(3,4-methylenedioxybenzyl)-piperazine.

40. A compound as in claim 1 which is 1-diphenylmethyl-3-methyl-3-(3,4-ethylenedioxybenzyl)-4-methylpiperazine.

41. A compound as in claim 1 which is (D)-1-diphenylmethyl-3-methyl-3-(3,4-ethylenedioxybenzyl)-4-methylpiperazine.

42. A compound as in claim 1 which is (L)-1-diphenylmethyl-3-methyl-3-(3,4-ethylenedioxybenzyl)-4-methylpiperazine.

43. A compound as in claim 1 which is (D)-1-diphenylmethyl-3-methyl-3-(3,4-ethylenedioxybenzyl)-4-ethylpiperazine.

44. A compound as in claim 1 which is (L)-1-diphenylmethyl-3-methyl-3-(3,4-ethylenedioxybenzyl)-4-ethylpiperazine.

45. A compound as in claim 1 which is (D)-1-diphenylmethyl-3-methyl-3-(3,4-ethylenedioxybenzyl)-4-n-propylpiperazine.

46. A compound as in claim 1 which is (L)-1-diphenylmethyl-3-methyl-3-(3,4-ethylenedioxybenzyl)-4-n-propylpiperazine.

47. A compound as in claim 1 which is 1-(p-chlorophenyl-phenylmethyl)-3-methyl-3-(3,4-ethylenedioxybenzyl)-4-methylpiperazine.

48. A compound as in claim 1 which is (D)-1-(p-chlorophenyl-phenylmethyl)-3-methyl-3-(3,4-ethylenedioxybenzyl)-4-methylpiperazine.

49. A compound as in claim 1 which is (L)-1-(p-chlorophenyl-phenylmethyl)-3-methyl-3-(3,4-ethylenedioxybenzyl)-4-methylpiperazine.

50. A compound as in claim 1 which is (D)-1-(p,p'-dichlorodiphenylmethyl)-3-methyl-3-(3,4-ethylenedioxybenzyl)-4-methylpiperazine.

51. A compound as in claim 1 which is (L)-1-(p,p'-dichlorodiphenylmethyl)-3-methyl-3-(3,4-ethylenedioxybenzyl)-4-methylpiperazine.

52. A compound as in claim 1 which is 1-(p-fluorophenyl-phenylmethyl)-3-methyl-3-(3,4-ethylenedioxybenzyl)-4-methylpiperazine.

53. A compound as in claim 1 which is (D)-1-(p-fluorophenyl-phenylmethyl)-3-methyl-3-(3,4-ethylenedioxybenzyl)-4-methylpiperazine.

54. A compound as in claim 1 which is (L)-1-(p-fluorophenyl-phenylmethyl)-3-methyl-3-(3,4-ethylenedioxybenzyl)-4-methylpiperazine.

55. A compound as in claim 1 which is 1-(p,p'-difluorodiphenylmethyl)-3-methyl-3-(3,4-ethylenedioxybenzyl)-4-methylpiperazine.

56. A compound as in claim 1 which is (D)-1-(p,p'-difluorodiphenylmethyl)-3-methyl-3-(3,4-ethylenedioxybenzyl)-4-methylpiperazine.

57. A compound as in claim 1 which is (L)-1-(p,p'-difluorodiphenylmethyl)-3-methyl-3-(3,4-ethylenedioxybenzyl)-4-methylpiperazine.

58. A compound as in claim 1 which is 1-diphenylmethyl-3-methyl-3-(3,4-methylenedioxybenzyl)-4-methylpiperazine.

59. A compound as in claim 1 which is (D)-1-diphenylmethyl-3-methyl-3-(3,4-methylenedioxybenzyl)-4-methylpiperazine.

60. A compound as in claim 1 which is (L)-1-diphenylmethyl-3-methyl-3-(3,4-methylenedioxybenzyl)-4-methylpiperazine.

61. A compound as in claim 1 which is (D)-1-diphenylmethyl-3-methyl-3-(3,4-methylenedioxybenzyl)-4-ethylpiperazine.

62. A compound as in claim 1 which is (L)-1-diphenylmethyl-3-methyl-3-(3,4-methylenedioxybenzyl)-4-ethylpiperazine.

63. A compound as in claim 1 which is (D)-1-diphenylmethyl-3-methyl-3-(3,4-methylenedioxybenzyl)-4-n-propylpiperazine.

64. A compound as in claim 1 which is (L)-1-diphenylmethyl-3-methyl-3-(3,4-methylenedioxybenzyl)-4-n-propylpiperazine.

65. A compound as in claim 1 which is 1-(p-chlorophenyl-phenylmethyl)-3-methyl-3-(3,4-methylenedioxybenzyl)-4-methylpiperazine.

66. A compound as in claim 1 which is (D)-1-(p-chlorophenyl-phenylmethyl)-3-methyl-3-(3,4-methylenedioxybenzyl)-4-methylpiperazine.

67. A compound as in claim 1 which is (L)-1-(p-chlorophenyl-phenylmethyl)-3-methyl-3-(3,4-methylenedioxybenzyl)-4-methylpiperazine.

68. A compound as in claim 1 which is (D)-1-(p,p'-dichlorodiphenylmethyl)-3-methyl-3-(3,4-methylenedioxybenzyl)-4-methylpiperazine.

69. A compound as in claim 1 which is (L)-1-(p,p'-dichlorodiphenylmethyl)-3-methyl-3-(3,4-methylenedioxybenzyl)-4-methylpiperazine.

70. A compound as in claim 1 which is (D)-1-(p-fluorophenyl-phenylmethyl)-3-methyl-3-(3,4-methylenedioxybenzyl)-4-methylpiperazine.

71. A compound as in claim 1 which is (L)-1-(p-fluorophenyl-phenylmethyl)-3-methyl-3-(3,4-methylenedioxybenzyl)-4-methylpiperazine.

72. A compound as in claim 1 which is 1-(p,p'-difluorophenylmethyl)-3-methyl-3-(3,4-methylenedioxybenzyl)-4-methylpiperazine.

73. A compound as in claim 1 which is (D)-1-(p,p'-difluorophenylmethyl)-3-methyl-3-(3,4-methylenedioxybenzyl)-4-methylpiperazine.

74. A compound as in claim 1 which is (L)-1-(p,p'-difluorophenylmethyl)-3-methyl-3-(3,4-methylenedioxybenzyl)-4-methylpiperazine.

75. A pharmaceutical composition for the treatment of coronary cardiac diseases or vascular diseases such as peripheral and cerebral circulatory disturbances, which composition comprises a therapeutically effective amount of a compound or salt as in claim 1 in combination with a pharmaceutical carrier.

76. A method for treating coronary cardiac diseases or vascular diseases such as peripheral and cerebral circulatory disturbances in a patient suffering therefrom, which method comprises intravenously or intramuscularly administering a therapeutically effective amount of a compound or salt as in claim 1 to said patient.

* * * * *